United States Patent [19]

Taylor et al.

[11] Patent Number: 4,667,664

[45] Date of Patent: May 26, 1987

[54] BLIND HOLE TARGETING DEVICE FOR ORTHOPEDIC SURGERY

[75] Inventors: Harold S. Taylor; John C. Taylor, both of Memphis, Tenn.

[73] Assignee: Richards Medical Company, Memphis, Tenn.

[21] Appl. No.: 692,826

[22] Filed: Jan. 18, 1985

[51] Int. Cl.⁴ .............................................. A61F 5/04
[52] U.S. Cl. .......................... 128/92 VV; 128/92 YY
[58] Field of Search .......... 128/92 EB, 92 BC, 92 H, 128/92 R, 92 G, 92 E, 92 VV, 92 VJ, 92 YY

[56] References Cited

U.S. PATENT DOCUMENTS

| | | | |
|---|---|---|---|
| 3,765,034 | 10/1973 | Johnston | 128/92 EB |
| 3,814,089 | 6/1974 | Deyerle | 128/92 EB |
| 3,815,590 | 6/1974 | Deyerle | 128/92 EB |
| 3,945,377 | 3/1976 | Kronner | 128/92 EB |
| 4,037,592 | 7/1977 | Kronner | 128/92 EB |
| 4,103,683 | 8/1978 | Neufeld | 128/92 EB |
| 4,257,411 | 3/1981 | Cho | 128/92 EB |
| 4,418,422 | 11/1983 | Richter et al. | 128/92 EB |

Primary Examiner—Stephen C. Pellegrino
Assistant Examiner—C. W. Shedd
Attorney, Agent, or Firm—Pravel, Gambrell, Hewitt & Kimball

[57] ABSTRACT

The present invention relates to installation of orthopedic implants and, more particularly, to a device for locating blind holes in an implanted prostheses so that a screw for interlocking the prosthesis with surrounding bone can accurately be installed.

12 Claims, 10 Drawing Figures

BLIND HOLE TARGETING DEVICE FOR ORTHOPEDIC SURGERY

BACKGROUND OF THE INVENTION

It is an accepted surgical procedure to install devices known as intramedullary nails in order to stabilize femoral and tibial fractures. The surgical technique of repairing such a fracture includes installing a prosthetic device known as an intramedullary nail in the medullary canal of the bone and locking it in place by means of self-tapping screws driven through holes located at both the distal and proximal ends of the nail for anchoring the nail in the surrounding bone.

This type of intramedullary fixation has been found effective for proximal and distal third shaft fractures, severely comminuted spiral and segmental fractures, non-unions and malunions between adjacent bone sections and bone lengthening where the fracture involves bone loss. By anchoring the intramedullary nail at both ends, the tendency for portions of the bone on adjacent sides of the fracture to rotate relative to each other is prevented and the length of the bone is maintained.

When a patient has a fracture complicated enough to require an interlocking intramedullary nail, the patient is positioned properly and an incision is made near the proximal end of the bone. The medullary canal is reamed and the intramedullary nail is introduced using known techniques.

The intramedullary nail is inserted into the bone, the nail being large enough to completely fill the intact medullary canal. A typical nail has two screw holes in its distal end and one in its proximal end so that self-tapping screws can be inserted for anchoring the nail to the bone. As can be appreciated, once the intramedullary nail has been installed in the bone, these holes cannot be visually observed by the physician and they must be located before the screws can accurately be inserted through the surrounding bone. An accepted technique for inserting the screw at the proximal end is to mount a fixture on the exposed end of the intramedullary nail with a drill guide that is aligned with the hole in the nail so that a guide hole can be drilled through the bone, through which the screw is inserted. Since the proximal screw hole is relatively close to the proximal end of the nail, this procedure is relatively uncomplicated.

However, for the two blind holes at the distal end of the nail, their distance from the proximal end is sufficiently great that it is difficult to locate them accurately. The importance of accurate location is apparent since before a locking screw can be inserted through these holes, a hole has to be drilled in the bone. Accurate location is therefore important to prevent trial and error location of the blind holes and unnecessary holes in the bone, which cause apparent problems.

Several techniques have been developed for locating these blind holes so that a guide hole can be accurately drilled in the bone for insertion of locking screws. All of these techniques involve the use of X-ray machines so that the physician can determine where the hole is located relative to the outer surface of the patient's leg. The difficulty of accurately locating the holes so that an incision can be made and an accurately located guide hole drilled in the bone is to determine the correct orientation of the blind hole relative to the outer skin of the patient. This problem is exacerbated by the fact that X-ray machines are two-dimensional so that even though the blind hole appears on an exposed X-ray plate, the physician cannot be certain of the axial orientation of the blind hole. If the guide hole is not co-axial with the blind hole axis, the anchoring screw cannot fit through the blind hole in the nail.

A serious problem in connection with locating these blind holes involves the fact that for each of these techniques a physician must be exposed to radiation from the X-ray machine while attempting to locate the holes. Overexposure to such radiation is dangerous to the physician and if a physician is exposed beyond predetermined safe levels, he or she would have to curtail the number of operations or stop operating on these types of fractures or face the possibility of serious health risks. Although lead-lined gloves have been developed for shielding the physician's hand and arm from harmful radiation, these are bulky and clumsy to use and many physicians believe that they hamper the physician's tactile effectiveness in performing the operation.

One technique that has been used for locating these blind holes in the distal end of an intramedullary nail is called a free-hand technique where the tip of a surgical instrument such as an awl is centered over the hole as determined with the aid of an X-ray machine. The shaft of the awl is moved until it is aligned with the X-ray beam while maintaining the tip of the awl in its original location at the opening of the hole. It has been found that this free-hand technique is not consistently accurate because the surgeon's hand oftentimes moves, especially when the awl is in contact with the slippery sloped surface of exposed bone. More importantly, however, is that the surgeon's hand is at times directly within the X-ray beam. Unless a surgeon is particularly skilled and can locate the axis of the blind hole quickly, overexposure to radiation can be a significant problem. Additional extension instruments have been developed to allow the surgeon to maintain the position of the awl through remote manipulation, but these extensions add additional instability to the system. Further, after the hole in the distal end of the intramedullary nail is located it must often times be relocated for drilling and screw insertion. This adds extra time to the operation.

A second technique has been developed that uses a targeting device that is fixed at the proximal end of the intramedullary nail and includes an arm that extends generally parallel to the nail. The arm has a joint in it so that it can pivot relative to the nail. However, the lever arm is relatively long and deflection can occur, which does not allow for precise location of the axis of the blind hole. Although the axis of the hole can be determined, there is some trial and error involved since the technique does not involve a predetermined sequence of steps; instead, the motions are complex with several degrees of freedom being manipulated simultaneously. Thus, unless a surgeon is particularly skilled, this procedure can be time consuming.

A third technique involves the use of a targeting device located on the C-arm of an X-ray machine. This device enables the surgeon to locate the axis of the screw hole, but there is no provision for a fine adjustment and the entire C-arm must be moved in order to accurately locate the hole, which is awkward in an operating room.

SUMMARY OF THE INVENTION

An apparatus for targeting the axis of a blind screw hole located in the distal end of an intramedullary nail implanted in a patient has been developed that includes a frame capable of being fixed on the proximal end of the intramedullary nail, on which a target mechanism is mounted. The target mechanism includes an alignment member with an axis that, through movement in four degrees of freedom, can be aligned co-axially with the blind hole. The target mechanism can be moved independently in at least four degrees of freedom relative to the axis of the blind hole. Movement in one of the degrees of freedom enables the alignment axis to intersect a plane that passes through the blind hole axis, while movement in a second degree of freedom enables the alignment axis to intersect a point located along the blind hole axis. Movement in the other two degrees of freedom enables the alignment axis and blind hole axis to be ultimately co-axial so that a guide hole can accurately be drilled in surrounding bone for insertion of a screw through the blind hole.

The target mechanism is formed to work with standard X-ray equipment and includes a platform formed of radioluscent material with perpendicular cross-hairs formed of radiodense material. Movement of the target mechanism as described above can be tracked through the use of the X-ray equipment to where the cross-hairs are centered on the blind hole and can be seen on an exposed X-ray plate.

The frame is formed with a support leg that is adapted to be connected perpendicular to the exposed proximal end of the intramedullary nail. A transverse arm is mounted perpendicular to the support leg and the target mechanism is mounted on the transverse arm, so that the arm is parallel to the nail.

After the frame has been mounted on the intramedullary nail and the target mechanism is in the general location of the blind hole, the transverse arm is adjusted through telescopic sections so that the alignment axis intersects first, a centering plane containing the blind hole axis, which is determined when one of the cross-hairs intersects the center of the blind hole. The frame also includes a slide mounted perpendicular to the transverse arm for moving the target mechanism so that the alignment axis is moved to where it intersects a point along the blind hole axis by centering both cross-hairs on the blind hole.

However, the axis of the hole cannot be determined by the cross-hairs alone, they may only be located on a single point along the blind hole axis, the physician not being sure whether the alignment axis is co-axial with the blind hole axis. In order to provide this additional information so that the physician can accurately drill a starter hole for the self-tapping screw that is co-axial with the blind hole, the target mechanism further includes an alignment column also formed of radioluscent material that is mounted on the platform perpendicular to the cross-hairs. The column includes a centering point formed of radiodense material spaced from the intersection of the cross-hairs for defining the alignment axis between the centering point and the intersection of the cross-hairs.

In order to accurately determine the orientation of the blind hole axis, the platform can be rotated about two axes, perpendicular to each other. Rotating the platform about the two axes can move the alignment axis to where it is positioned co-axial with the blind hole axis, as determined by the centering point being centered over the blind hole.

The alignment column includes an opening co-axial with the alignment axis, the centering point being formed as part of a removable plug which, when removed, enables a drill guide to be inserted in the opening so that a starter hole can be accurately drilled in the bone and through the blind hole. In this way, the hole can accurately be located so that inaccurately placed holes will not be drilled in the patient's bone.

The apparatus just described when properly used is intended to significantly reduce the time it takes to locate the axis of the blind hole, which translates directly into reduced radiation exposure to the physician. The frame also provides a stable platform for holding a drill guide so that an accurate hole can be drilled in the bone. Furthermore, by providing four independent degrees of motion, if the frame should shift in one direction, the alignment axis can easily be realigned with the blind hole axis.

BRIEF DESCRIPTION OF THE DRAWINGS

A better understanding of the invention can be obtained when the detailed description of an exemplary embodiment set forth below is considered in conjunction with the following drawings, in which.

DETAILED DESCRIPTION OF AN EXEMPLARY EMBODIMENT

Figure 1:
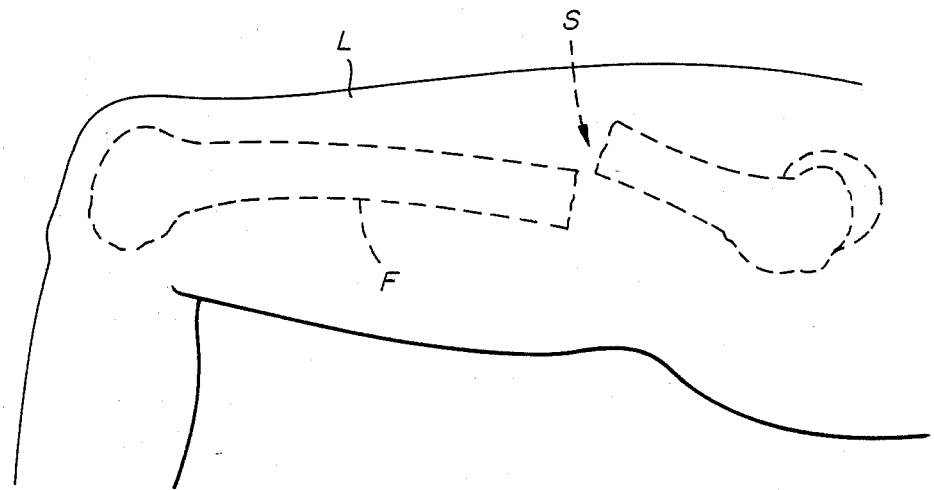
FIG. 1 is a perspective view, partially in section, showing a fracture of a femur.

Referring to the drawings, the invention as illustrated relates to a surgical technique for repairing a fracture of one of the long bones of a patient. The invention will be described in conjunction with a fracture in the femur, but it can be used in conjunction with implants that are used for the repair of fractures in other bones. Referring to FIG. 1, upper leg L is shown in which a femur F has been fractured, as shown at fracture site S, and are out of alignment with each other.

Figure 2:
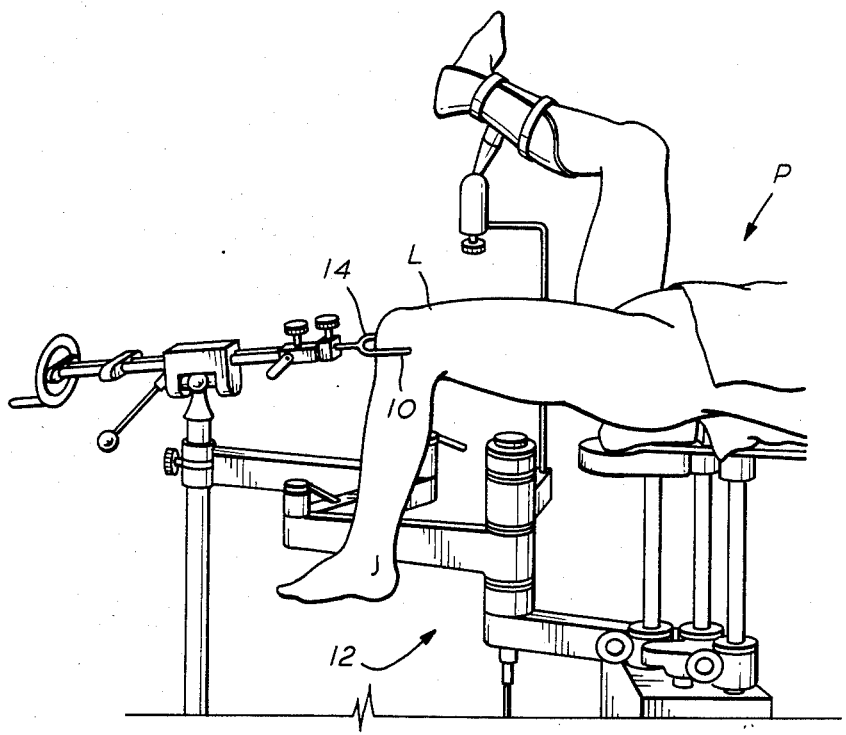
FIG. 2 is a perspective view illustrating positioning of a patient.

As shown in FIG. 2, the patient P is placed in a supine position and the leg L is stabilized by fixing a femoral transcondlyar sterile Steinmann pin 10 to the distal end of the femur (not shown) by an accepted technique, the Steinmann pin 10 being affixed to an orthopedic table generally designated by reference numeral 12 through a rigid stirrup 14. The patient is positioned so that the leg L is accessible to an image intensifier or X-ray machine (not shown) at various angles.

Figure 3:
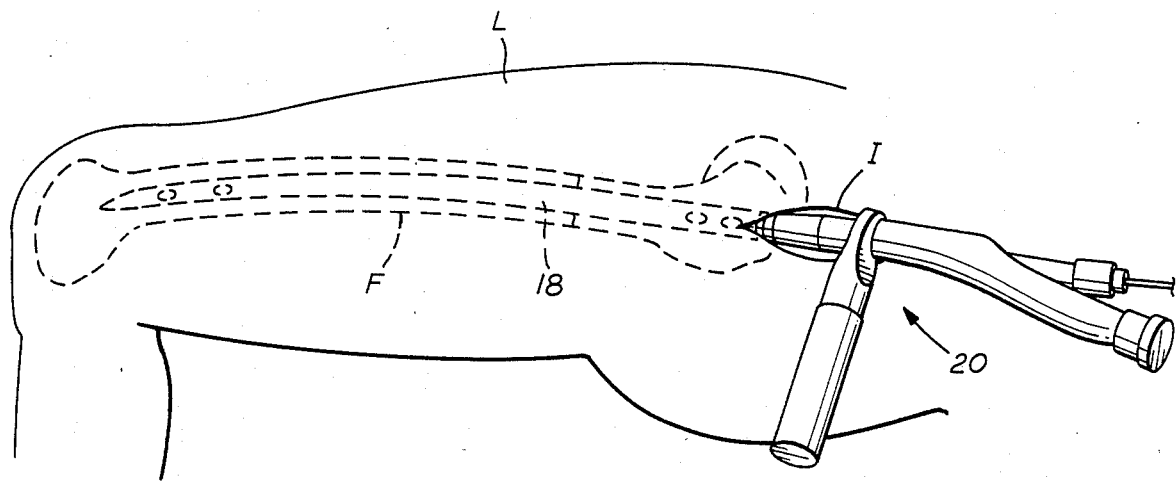
FIG. 3 is a perspective view, totally in section, showing a portion of the surgical procedure for implanting an intramedullary nail.
Figure 4:
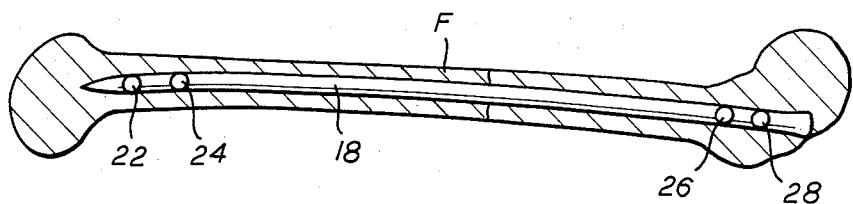
FIG. 4 is a perspective view of a femur in which an intramedullary nail has been implanted.

Typically, in order to reduce or set the fracture and prepare the femur for receiving an intramedullary nail 18, an incision I is formed through which the medullary canal of the femur is opened at the proximal end of the femur F as shown in FIG. 3. A standard surgical technique is used for reducing or setting the fracture so that the broken portions are returned to the position shown in FIG. 3. After the fracture is reduced, the intramedullary canal of the femur F is reamed about 1 millimeter larger than the diameter of the nail that is to be implanted. As shown in FIG. 3, the nail 18 is introduced by means of a driver extractor device 20, using a known surgical technique. After the nail 18 has been inserted into the femur F to the position shown in FIG. 4, the driver extractor 20 is removed.

Figure 5:
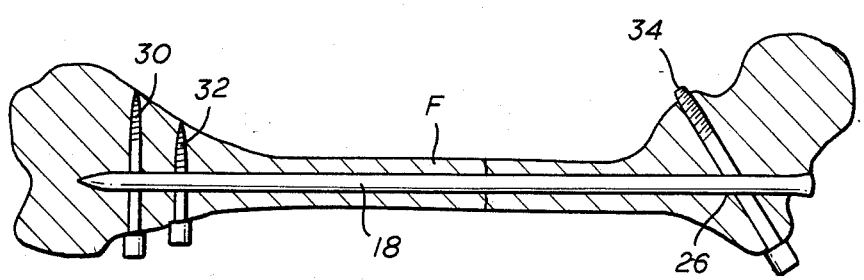
FIG. 5 is a perspective view, partially in section, showing the femur of FIG. 4 rotated 90° in which the intramedullary nail has been locked in place by use of fixation screws.

The intramedullary nail 18 is provided with guide holes 22, 24 in its distal end and 26, 28 in its proximal end for receiving appropriate fixation screws (see FIG. 5) for anchoring the intramedullary nail 18 in place. This type of fixation operates to prevent the portions of the bone on either side of the fracture site from moving relative to each other and to prevent the nail from rotating. As shown in FIG. 5 (rotated 90° relative to the view shown in FIG. 4) self-tapping screws 30, 32 are used to connect the intramedullary nail 18 to the femur F through the holes 22, 24, respectively. A self-tapping screw 34 anchors the proximal end of the intramedullary nail 18, passing through proximal hole 28. The other hole 26 in the proximal end of the intramedullary nail 18 is formed to intersect the hole 28 and is used for anchoring the intramedullary nail 18 when used for fractures of the other leg.

The foregoing description of insertion of the intramedullay nail 18 is merely a summary of the overall surgical procedure, which can be a complicated and time-consuming operation. As can be appreciated, once the intramedullary nail 18 has been inserted in the femur F, the holes 22, 28 cannot be observed by the physician and must be located as blind holes before the screws 30–34 can be inserted.

For insertion of the screw 34, since the hole 28 is located close to the proximal end of the intramedullary nail 18, the hole 28 can relatively easily be located by mounting a proximal siting device (not shown) on the proximal end of the nail 18, which includes a drill guide that is aligned with the hole 28. In this way, a small incision can be made and a hole drilled in the femur F for starting the screw 34. The same drill guide can also be used for positioning the screw and avoiding misalignment during insertion. By mounting the siting device on the proximal end of the nail 18, the guide is positioned in precise alignment with the hole 28. However, since the holes 22, 24 are located on the distal end of the nail 18 a distance of about 36–48 centimeters from the exposed proximal end, it is much more difficult to locate the axes of the holes 22, 24.

Figure 6:
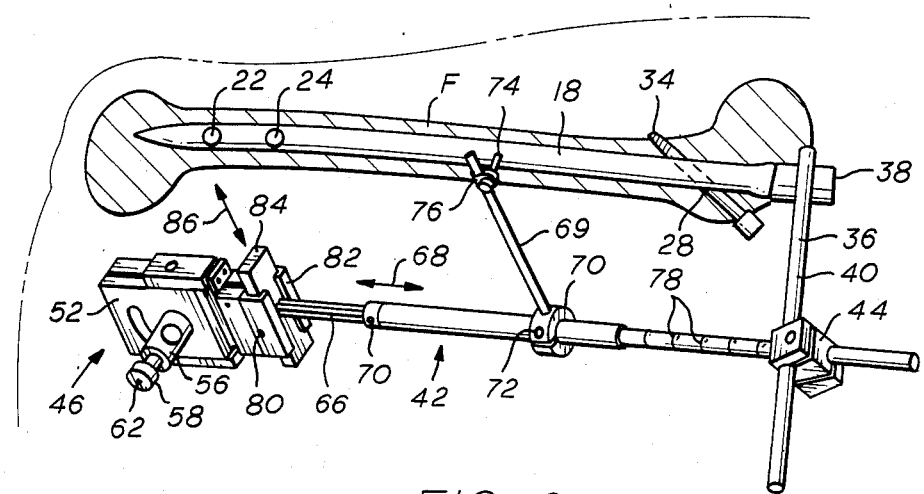
FIG. 6 is a perspective view, partially in section, showing in particular the apparatus of the present invention mounted on the proximal end of the intramedullary nail in position for aligning a drill guide with the axis of one of the distal blind holes of the nail.

In order to permit the physician to make such an alignment, a blind hole targeting device shown in FIG. 6 has been developed. This device eliminates the need for the surgeon to expose his or her hand and arm to radiation needlessly and at the same time provide accurate location of the blind holes so that unnecessary holes are not drilled into the femur F in wrong locations. The device is used in conjunction with an X-ray machine (not shown) that is necessary in determining the location of the blind holes and the relative orientation of a targeting mechanism relative to a blind hole. The device is designed so that the surgeon is not exposed to needless amounts of radiation, but at the same time provide accurate alignment so that a guide hole can be drilled along the axis of a blind hole without the need for trial and error.

The device includes an alignment opening with an axis (e.g., alignment axis) that needs to be co-axial with the blind hole before a guide hole can accurately be drilled. As described below, the alignment opening can accommodate a drill guide so that such a guide hole can be formed with no further adjustments after the alignment axis is co-axial with the blind hole.

In has been determined that in order to accurately locate the axis of a blind hole such as holes 30, 32, the alignment axis device must be capable of independent movement through at least four degrees of freedom. In order to understand the term "degrees of freedom," as used in this description, it should be appreciated that any object may be translated along three mutually perpendicular axes. The object may also be rotated about three mutually perpendicular axes. Thus, any complex motion of an object is the result of a combination of motions, translational and rotational, along about three mutually perpendicular axes. The ability to rotate or translate about these axes is defined as a "degree of freedom, " resulting in six possible degrees of freedom for any object. As described below, two of the six degrees of freedom are not necessary to determine the axis of a blind hold. Thus, in order to locate a blind hole axis, a device must be capable of moving a targeting mechanism along at least four degrees of freedom.

Movement in two degrees of freedom as described is designed to move the alignment axis where it intersects a point along the blind hole's axis. Once this point is determined, the blind hole axis is not completely determined since the orientation of the hole is determined by four degrees of freedom. Therefore, in order to make sure that the alignment axis is co-axial with the blind hole, the device must be capable of moving through two additional degrees of freedom. These independent motions as well as the targeting device are described in greater detail below.

As shown in FIG. 6, the targeting device includes a support leg 36 that is mounted at one end to the distal end of the intramedullary nail 18 through complementary fitting slots (not shown) and a locking device 38. The complementary slots insure that the support leg 36 is mounted relative to the intramedullary nail 18 in a predetermined orientation. The support leg 36 also includes a guide opening 40 that can be used for locating the axis of the proximal hole 28 for insertion of the proximal screw 34 as shown. However, since other devices are provided for performing this operation, this feature is not part of the invention other than as an additional feature.

Figure 10:
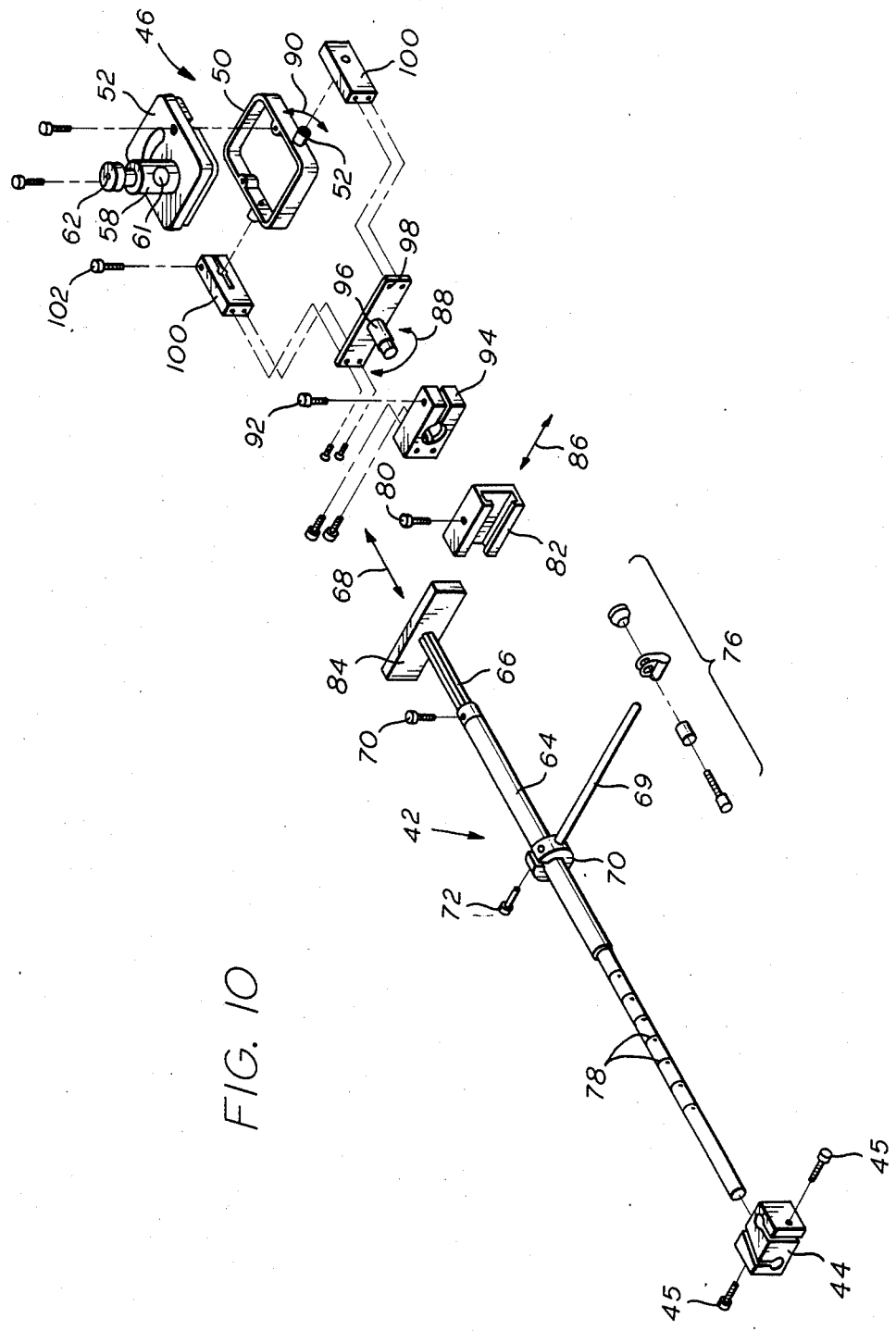
FIG. 10 is an exploded perspective view of the apparatus of the present invention.

As shown in FIGS. 6, 10, a transverse support arm designated generally by reference numeral 42 is mounted on the support leg 36 through a mounting block 44 in which set screws 45 are used to tighten slots for holding the support leg 36 and transverse arm 42 tightly in place. With the support leg 36 being mounted on the proximal end of the nail 18 in a predetermined orientation and the support block 44 providing a similar predetermined orientation between the support leg 36 and transverse arm 42, the arm 42 is mounted generally parallel to the nail 18.

Hash markings 78 are formed on the transverse arm 42 to indicate generally the distances between the distal end of the nail 18 and one of the blind holes (hole 24, as shown in FIG. 6) so that the targeting portion of the device can be roughly aligned with the axis of the blind hole 24. The targeting device is used to align the alignment axis co-axial with the blind hole as described below.

After the transverse support arm 42 is locked in place in the support block 44, a stabilizing arm 69 mounted to the transverse support arm 42 through a split ring 70 tightened by a set screw 72 can be moved to the position shown in FIG. 6 where a fixation pin 74, inserted through a pin holding portion generally designated by referenced numeral 76, is connected to the femur F for providing extra stability to the transverse support arm 42.

A target mechanism 46 is mounted on the distal end of the transverse arm 42 in a manner described in detail below. The target mechanism 46 is shown in detail in FIGS. 7 and 8 and includes a platform 48 that is formed of an outer frame 50 that surrounds and holds a tray 52 formed of radioluscent material. A set of perpendicular cross-hairs 54a, 54b formed of a radiodense material is mounted in the radioluscent material so that when the cross-hairs appear on an exposed X-ray plate, the material in which they are embedded do not.

Figure 7:
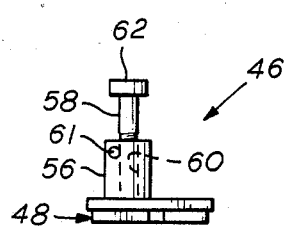
FIG. 7 is a side view of the target mechanism of the apparatus shown in FIG. 6.
Figure 8:
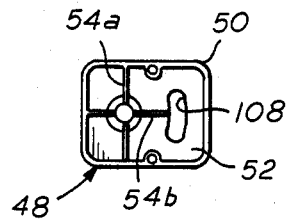
FIG. 8 is a top view of the platform portion of the targeting mechanism of FIG. 7.

An alignment guide 56, also formed of a radioluscent material, is mounted on the platform 48 as shown in FIGS. 7, 10, with a removable plug 58 designed to be fitted within a longitudinal guide opening 60 formed along the interior of the alignment guide 56. A set screw 61 holds the plug 58 in place when targeting a blind hole.

The plug 58 is also formed of a radioluscent material and includes a centering ball 62 formed of radiodense material, that is located along the axis of the longitudinal opening 60, which also intersects the intersection point of the cross-hairs 54a, 54b. The axis of the opening 60 forms the alignment axis of the targeting apparatus for locating the axis of a blind hole, as described in greater detail below.

The transverse support arm 42 includes two telescoping sections 64, 66 so that the targeting mechanism 46 can be moved back and forth in the direction of arrows designated by reference numeral 68 to a point where the cross-hair 54a intersects the center of the blind hole 24. This is done by sliding the section of the transverse arm 64 in the direction of arrow 68 until the cross-hair 54a is centered over the blind hole 24, as shown on an exposed X-ray plate. After this position is reached, a set screw 70 is tightened for locking the targeting mechanism 46 in that position.

The capability of the transverse arm 42 to move the targeting mechanism 46 back and forth in the direction of the arrow 68 is the first degree of freedom mentioned above that is used to align the alignment axis with the axis of the blind hole 24.

After the cross-hair 54a is centered on the blind hole 24, and the transverse arm 42 is locked against any further movement in a direction of the arrow 68, a set screw 80 mounted on slide piece 82 which slides along piece 84 is loosened for enabling the cross-hair 54b to be moved relative to the center of the blind hole 24 in the direction of arrows 86. As the cross-hair 54b moves in this direction, the cross-hair 54a remains centered over the blind hole 24. When the cross-hair 54b is centered on the blind hole 24, the set screw 80 is locked to prevent the holder 82 and slide piece 84 from any further relative movement. By aligning the cross-hairs 54a and 54b on the center of the blind hole 24, movement of the alignment axis in the two degrees of freedom just described enabled it to intersect a point along the axis of the blind hole, the alignment axis not necessarily being co-axial with the blind hole axis.

As shown best in FIG. 10, the target mechanism and accordingly the alignment axis are capable of rotational movement in two directions relative to the transverse support arm 42, in the direction of rotational arrows designated by reference numerals 88, 90, respectively. In order to rotate the target mechanism in the direction of the arrows 88, a set screw 92 is loosened, at which time the alignment axis along the ball 62 and intersection of the cross-hairs 54a, 54b rotates until the ball 62 intersects cross-hair 54b, as determined by an exposed X-ray plate. The set screw 92 is located in a holding block 94 in which a shaft 96 mounted on a bar 98 is located. The platform 48 is mounted to the bar 98 through end supports 100 that are mounted on the platform frame 50 through rods 52.

While the targeting mechanism 46 is being moved in the direction of the arrows 88, it is locked against movement in the directions of the arrows 68, 86 for preventing the alignment axis from moving out of the previous alignment positions described above. After the alignment axis is centered through movement in the direction of the arrows 88, the set screw 92 is tightened for preventing any further movement in that direction.

In order to enable the targeting mechanism 46 to move through the fourth degree of freedom for aligning the alignment axis co-axial with the blind hole 24, a set screw 102 located in one of the end blocks 100 is loosened for allowing the platform 48 to rotate in the direction of the arrows 90. During this movement of the platform 48, movement in the other three degrees of freedom discussed above is fixed so that the alignment axis will move into co-axial orientation relative to the axis of the blind hole 24, as determined by an exposed X-ray plate. This final position is determined by centering the ball 62 and cross-hair intersection on the center of the blind hole 24 and provides co-axial alignment between the alignment axis and the blind hole 24.

After this final alignment is realized, the plug 58 is removed from the longitudinal opening 60 after loosening the set screw 61 and a drill guide 106 (see FIG. 9) is inserted in the longitudinal opening 60 for guiding a power drill in order to form a guide hole in the femur F along the axis of the blind hole 24 in order to facilitate insertion of the fixation screw 32 (see FIG. 5).

Figure 9:
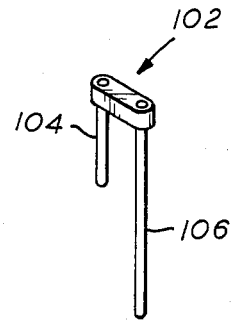
FIG. 9 is a drill guide for the second of the blind distal holes of the intramedullary nail of the type shown in FIG. 6.

After the fixation screw 32 is inserted in accordance with accepted procedures, the drill guide is removed from the longitudinal opening 60 and a spaced adaptive drill guide 102 shown in FIG. 9 is inserted for installing the fixation screw 30 in the blind hole 22. A guide leg 104 is inserted in the longitudinal opening 60, the drill guide 106 passing through a slot 108 formed in the platform 48 and being locked in place once it is centered over the second blind hole 22. The drill guide 106 then operates to guide an automatic drill for forming a guide hole in the femur F in order to facilitate insertion of the fixation screw 30. After both of the fixation screws 30, 32 are inserted, the fixation pin 74 is removed and the support leg 36 is disconnected from the intramedullary nail 18. The operation can then be completed by the physician.

As described in the foregoing detailed description, the apparatus of the present invention provides a blind hole targeting device for orthopedic surgery that enables blind holes in orthopedic implants to be located with facility and accuracy. The device described significantly reduces the time it takes to locate a blind hole in an implant and can be used in conjunction with conventional X-ray equipment in such a way that the length of time that a physician is exposed to dangerous radiation is reduced significantly. It also substantially reduces the risk of missing the blind hole and drilling needless other holes in a patient's bone, which can have the unfortunate effect of weakening the bone and complicating surgery.

It should be understood that variations and improvements can be made to the foregoing invention without departing from the spirit of the invention, all such variations and improvements are being contemplated as coming within the scope of the invention as defined in the appended claims.

We claim:

1. An apparatus for targeting the axis of a blind hole in an orthopedic implant, comprising:
   (a) a frame,
   (b) target means mounted on the frame, including an alignment means with an axis capable of being moved co-axial with the axis of the blind hole,
   (c) mounting means for mounting the frame in a fixed position relative to the blind hole;
   (d) adjustment means for enabling the target means to move independently in at least four degrees of freedom relative to the axis of the blind hole, movement in two of the degrees of freedom enabling the alignment means axis to respectively intersect a plane containing and a point along the blind hole axis, and movement in two other degrees of freedom enabling the alignment means axis and blind hole axis to be made respectively co-planar and co-axial.

2. The apparatus of claim 1, wherein the frame includes a support leg and means for connecting the support leg to an exposed portion of the implant.

3. The apparatus of claim 2, wherein the frame includes an arm, means for mounting the arm on the support leg, the targeting means being mounted on the arm.

4. The apparatus of claim 3, wherein the implant is formed as an elongated intramedullary nail, the support leg being mounted perpendicular to the longitudinal axis of the intramedullary nail and the arm being mounted perpendicular to the support leg and parallel to the longitudinal axis of the nail.

5. The apparatus of claim 3, wherein the adjustment means includes telescoping sections on the arm.

6. The apparatus of claim 3, wherein the adjustment means includes transverse slide means mounted on the arm.

7. The apparatus of claim 4, wherein movement of one of the telescoping sections and transverse slide means can move the alignment means axis to intersect a plane containing the blind hole axis and thereafter movement of the other of the telescoping sections and transverse slide means can move the alignment means axis to intersect a point along the blind hole axis.

8. The apparatus of claim 1, wherein the target means includes a platform formed of radioluscent material and perpendicular cross-hairs formed of radiodense material.

9. The apparatus of claim 8, wherein the alignment means includes an alignment guide formed of radioluscent material mounted on the platform perpendicular to the cross-hairs, the guide including a centering point formed of radiodense material spaced from the intersection of the cross-hairs to form the alignment means axis.

10. The apparatus of claim 7 or 9, wherein the target means includes first rotating means for rotating the platform in a first degree of freedom so that the alignment means axis is co-planar with the blind hole axis after the alignment means axis has been moved to intersect a point along the blind hole axis.

11. The apparatus of claim 10, wherein the targeting means includes second rotating means for rotating the platform in a second plane so that after the first rotating means has moved the alignment means axis to intersect a plane along the blind hole axis the alignment means axis can be moved co-axial with the blind hole.

12. The apparatus of claim 9, wherein the alignment guide and platform include an opening co-axial with the alignment means axis, the centering point being formed as part of a removable member for enabling a drill guide to be inserted in the opening.

* * * * *